United States Patent [19]

Nishi et al.

[11] 4,277,479
[45] Jul. 7, 1981

[54] TETRAZOLYLALKOXYCARBOSTYRIL DERIVATIVES AND PHARMACEUTICAL COMPOSITIONS CONTAINING THEM

[75] Inventors: Takao Nishi; Kazuyuki Nakagawa, both of Tokushima, Japan

[73] Assignee: Otsuka Pharmaceutical Co., Ltd., Tokyo, Japan

[21] Appl. No.: 70,710

[22] Filed: Aug. 29, 1979

[30] Foreign Application Priority Data

Sep. 1, 1978 [JP] Japan .................. 53/107869

[51] Int. Cl.³ .................. A61K 31/47; C07D 401/12
[52] U.S. Cl. .................. 424/258; 546/157; 546/158; 548/250
[58] Field of Search .................. 546/157, 158; 424/258

[56] References Cited

U.S. PATENT DOCUMENTS

| | | | |
|---|---|---|---|
| 2,470,084 | 5/1949 | Harvill et al. | 548/252 X |
| 2,470,085 | 5/1949 | Harvill et al. | 548/252 X |
| 3,919,239 | 11/1975 | Nakagawa et al. | 424/258 X |
| 4,070,470 | 1/1978 | Nakagawa et al. | 424/258 |
| 4,072,683 | 2/1978 | Nakagawa et al. | 424/258 X |
| 4,129,565 | 12/1978 | Fukushima et al. | 424/258 X |
| 4,210,753 | 7/1980 | Tominaga et al. | 546/157 X |

FOREIGN PATENT DOCUMENTS 54-30183  3/1979  Japan .

*Primary Examiner*—Donald G. Daus
*Assistant Examiner*—Diana G. Rivers

[57] ABSTRACT

Novel tetrazolylalkoxycarbostyril derivative of the formula (I):

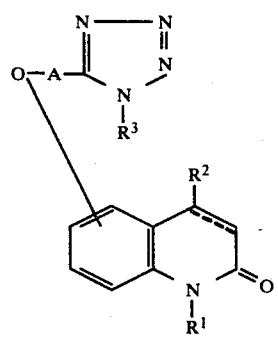

wherein $R^1$ is a hydrogen atom, a lower alkyl group, a low alkenyl group, a lower alkanoyl group, a benzoyl group or phenylalkyl group; $R^2$ is a hydrogen atom, a lower alkyl group or a group of the formula

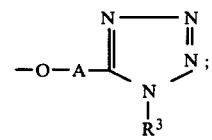

$R^3$ is a lower alkyl group, a cycloalkyl group, a cycloalkylalkyl group, a phenyl group or a phenylalkyl group; A is a lower alkylene group; the carbon-carbon bond between 3- and 4-positions in the carbostyril skeleton is either single or double bond; and the substituted position of a group of the formula,

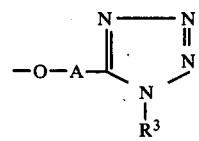

in the carbostyril skeleton is either 4-, 5-, 6-, 7- or 8-position provided that the only one such group of the formula can be substituted in the whole carbostyril skeleton, thus when $R^2$ in 4-position is a group of the formula

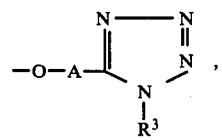

then 5-, 6-, 7- or 8-position will have no such substituted group; furthermore, the phenyl group in the above-mentioned benzoyl group, phenylalkyl group or phenyl group may have substituted group(s).

The above-mentioned novel tetrazolylalkoxycarbostyril derivatives have pharmacological activities such as platelet aggregation inhibitory action, antiinflammatory action, antiulcer action, vasodilatory action and phosphodiesterase inhibitory action and are useful as antithrombosis agent, cerebral blood flow improving agent, antiinflammatory agent, antiulcer agent, anti-hypertensive agent and anti-asthmatic agent.

28 Claims, No Drawings

TETRAZOLYLALKOXYCARBOSTYRIL DERIVATIVES AND PHARMACEUTICAL COMPOSITIONS CONTAINING THEM

The present invention relates to novel tetrazolylalkoxycarbostyril derivatives and process for producing the same and to a pharmaceutical composition.

It is known that certain carbostyril derivatives exhibit useful pharmacological activities. For example, 5-(2'-hydroxy-3-tert-butylamino)-propoxy-3,4-dihydrocarbostyril having the formula

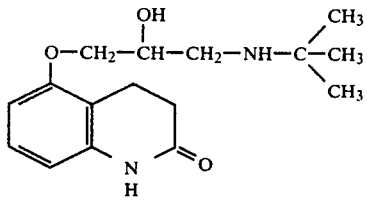

at low concentration could specifically inhibit the aggregation of blood platelets and this compound is very effective for preventing and treating thrombosis when administered orally or intravenously to mammals including humans [Japanese Patent Kokai (Laid-open) No. 125,930/73].

Additionally, several carbostyril derivatives disclosed in Japanese Patent Kokai (Laid-open) Nos. 106977/1975, 142576/1975, 116482/1977 and 30183/1979 show some useful pharmacological activities for example, inhibitory effect of aggregation of blood platelets, inhibiting effect of phosphodiesterase, antiulcer effect, antiinflamatory effect and vasodilatory effect.

An object of the present invention is to provide novel tetrazolylalkoxycarbostyril derivatives which have excellent inhibitory action of platelet aggregation, antiinflamatory action, antiulcer action, vasodilatory action and phosphodiesterase inhibitory action.

Another object of the present invention is to provide a process for producing such novel tetrazolylalkoxy carbostyril derivatives.

A further object of the present invention is to provide a pharmaceutical composition containing the novel tetrazolylalkoxy carbostyril derivative as an active ingredient.

According to the present invention, there are provided novel tetrazolylalkoxycarbostyril derivatives represented by the general formula (I),

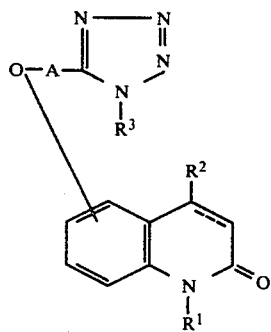

wherein $R^1$ is a hydrogen atom, a lower alkyl group, a lower alkenyl group, a lower alkanoyl group, a benzoyl group or a phenylalkyl group; $R^2$ is a hydrogen atom, a lower alkyl group or a group of the formula

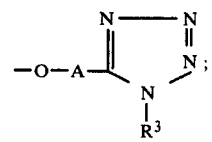

$R^3$ is a lower alkyl group, a cycloalkyl group, a cycloalkylalkyl group, a phenyl group or a phenylalkyl group; A is a lower alkylene group; the carbon-carbon bond between 3- and 4-positions in the carbostyril skeleton is either single or double bond; and the substituted position of the group represented by the formula,

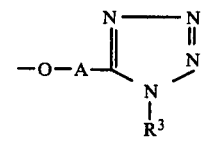

in the carbostyril skeleton is either 4-, 5-, 6-, 7- or 8-position provided that only one such group of the formula can be substituted in the whole carbostyril skeleton, thus when $R^2$ in 4-position is

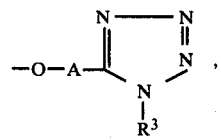

then 5-, 6-, 7- or 8- position will have no such substituted group; furthermore the phenyl group in the above-mentioned benzoyl group, phenylalkyl group or phenyl group may have substituted group(s).

The compounds of the present invention have a platelet aggregation inhibitory action, antiinflammatory action, antiulcer action, vasodilatory action and phosphodiesterase (PDE) inhibitory action and are useful an anti-thrombosis agents, cerebral blood flow improving agents, antiinflammatory agents, antiulcer agents, antihypertensive agents and anti-asthmatic agents.

Additionally, the compounds of the present invention have a relatively longer effective time in use for preventing or curing the above-mentioned diseases and with low toxicities as well as with relatively less side-effects relating to heart diseases such as tachycardia, myocardial insufficiency, etc.

In the general formula (I), the lower alkyl groups defined in $R^1$, $R^2$ and $R^3$ are represented by straight- or branched-chain alkyl groups having 1 to 4 carbon atoms, which may be more definitely specified as methyl, ethyl, propyl, isopropyl, butyl, isobutyl or tert-butyl groups or the like.

The lower alkenyl group defined in $R^1$ is represented by a straight- or branched-chain alkenyl group having 2 to 4 carbon atoms, which may be more definitely specified as vinyl, allyl, crotyl or 1-methylallyl group or the like.

The lower alkanoyl group defined in $R^1$ is represented by a straight- or branched-chain alkanoyl group having 1 to 4 carbon atoms, which may be definitely specified as formyl, acetyl, propionyl, butyryl or isobutyryl group or the like.

The phenylalkyl group defined in $R^1$ and $R^3$ is represented by a phenylalkyl group in which the straight- or branched-chain alkyl group having 1 to 4 carbon atoms, having one or more phenyl group(s), which may be definitely specified as benzyl, α-phenethyl, β-phenethyl, 3-phenylpropyl, 4-phenylbutyl, 1,1-dimethyl-2-phenylethyl, diphenylmethyl group or the like.

The cycloalkyl group defined in $R^3$ is represented by a cycloalkyl group having 3 to 8 carbon atoms, which may be definitely specified as cyclopropyl, cyclobutyl, cyclopentyl, cyclohexyl, cycloheptyl or cyclooctyl group or the like.

The cycloalkylalkyl group defined in $R^3$ is represented by a cycloalkylalkyl group in which the straight- or branched-chain alkyl group having 1 to 4 carbon atoms, having one or more cycloalkyl group(s), which may be definitely specified as cyclopropylmethyl, cyclobutylmethyl, cyclopentylmethyl, cyclohexylmethyl, cyclooctylmethyl, dicyclohexylmethyl, 2-cyclohexylethyl, 2-cyclooctylethyl, 1-methyl-2-cyclohexylethyl, 3-cycloheptylpropyl, 4-cyclohexylbutyl, 1,1-dimethyl-2-cyclohexylethyl group or the like.

As to the substituted groups on the phenyl group in the said benzoyl group, phenylalkyl group and phenyl group, they may be definitely specified as lower alkoxy group(s) for example, methoxy, ethoxy, propoxy, isopropoxy, butoxy or tert-butoxy group(s); lower alkyl group(s) for example, methyl, ethyl, propyl, isopropyl, butyl, isobutyl or tert-butyl group(s); halogen atom(s) for example, chlorine, fluorine, bromine atom(s); di-lower alkylamino group(s) for example, dimethylamino, diethylamino, dipropylamino, dibutylamino or methylethylamino group(s); nitro group(s); lower alkylenedioxy group(s) for example, methylenedioxy, ethylenedioxy or trimethylenedioxy group(s).

The phenyl, phenylalkyl or benzoyl group having said substituted group(s) may be exemplified as a substituted phenyl group for example, 4-chlorophenyl, 3,5-dichlorophenyl, 2-bromophenyl, 4-methoxyphenyl, 3,4-dimethoxyphenyl, 2-nitrophenyl, 3,4,5-trimethoxyphenyl, 2-methylphenyl, 4-ethylphenyl, 3,4-dimethylphenyl, 3,4-methylenedioxyphenyl, 2-chloro-4-nitrophenyl or 4-dimethylaminophenyl group; a substituted benzoyl group for example, 4-chlorobenzoyl, 3,5-dichlorobenzoyl, 2-bromobenzoyl, 4-methoxybenzoyl, 3,4-dimethoxybenzoyl, 2-nitrobenzoyl, 3,4,5-trimethoxybenzoyl, 2-methylbenzoyl, 4-ethylbenzoyl, 3,4-dimethylbenzoyl, 3,4-methylenedioxybenzoyl, 2-chloro-4-nitrobenzoyl or 4-dimethylaminobenzoyl group; a substituted phenylalkyl group for example, 4-chlorobenzyl, 3,5-dichlorobenzyl, β-2-bromophenethyl, 4-methoxybenzyl, β-3,4-dimethoxyphenethyl, 2-nitrobenzyl, β-3,4,5-trimethoxyphenethyl, 2-methylbenzyl, α-4-ethylphenethyl, β-3,4-dimethylphenethyl, β-3,4-methylenedioxyphenethyl, 2-chloro-4-nitrobenzyl or β-4-dimethylaminophenethyl group.

Furthermore, the lower alkylene group defined as A in the general formula (I) is represented by a straight- or branched-chain alkylene group having 1 to 6 carbon atoms, which may be more definitely specified as methylene, ethylene, trimethylene, propylene, tetramethylene, 2-ethylethylene, pentamethylene, hexamethylene, 2-methyltrimethylene, 2,2-dimethyltrimethylene, or 1-methyltrimethylene group.

Listed below are representative examples of the compounds provided according to the present invention.

6-[3-(1-Methyltetrazol-5-yl)propoxy]carbostyril
6-[3-(1-Ethyltetrazol-5-yl)propoxy]carbostyril
6-[3-(1-Propyltetrazol-5-yl)propoxy]carbostyril
6-[3-(1-Isobutyltetrazol-5-yl)propoxy]carbostyril
6-[3-(1-Cyclopentyltetrazol-5-yl)propoxy]carbostyril
6-[3-(1-Cyclohexyltetrazol-5-yl)propoxy]carbostyril
6-[3-(1-Cyclobutyltetrazol-5-yl)propoxy]carbostyril
6-[3-(1-Cyclopropyltetrazol-5-yl)propoxy]carbostyril
6-[3-(1-Ethyltetrazol-5-yl)propoxy]-3,4-dihydrocarbostyril
6-[3-(1-Cyclohexyltetrazol-5-yl)propoxy]-3,4-dihydrocarbostyril
4-[3-(1-Ethyltetrazol-5-yl)propoxy]carbostyril
4-[3-(1-Cyclohexyltetrazol-5-yl)propoxy]carbostyril
6-[3-(1-Cyclohexyltetrazol-5-yl)propoxy]-4-methylcarbostyril
5-[3-(1-Cyclohexyltetrazol-5-yl)propoxy]carbostyril
7-[3-(1-Cyclohexyltetrazol-5-yl)propoxy]carbostyril
8-[3-(1-Cyclohexyltetrazol-5-yl)propoxy]carbostyril
5-[3-(1-Cyclohexyltetrazol-5-yl)propoxy]-3,4-dihydrocarbostyril
7-[3-(1-Cyclohexyltetrazol-5-yl)propoxy]-3,4-dihydrocarbostyril
8-[3-(1-Methyltetrazol-5-yl)propoxy]carbostyril
5-[3-(1-Ethyltetrazol-5-yl)propoxy]-3,4-dihydrocarbostyril
6-(1-Cyclohexyltetrazol-5-yl-methoxy)carbostyril
6-[2-(1-Cyclohexyltetrazol-5-yl)ethoxy]carbostyril
5-[4-(1-Cyclohexyltetrazol-5-yl)butoxy]carbostyril
6-[5-(1-cyclohexyltetrazol-5-yl)pentyloxy]carbostyril
7-[6-(1-Cyclohexyltetrazol-5-yl)hexyloxy]carbostyril
6-[4-(1-Cyclohexyltetrazol-5-yl)butoxy]-3,4-dihydrocarbostyril
1-Methyl-6-[3-(1-cyclohexyltetrazol-5-yl)propoxy]carbostyril
1-Ethyl-6-[3-(1-cyclopentyltetrazol-5-yl)propoxy]3,4-dihydrocarbostyril
1-Butyl-6-[3-(1-cyclohexyltetrazol-5-yl)propoxy]carbostyril
1-Isopropyl-7-[3-(1-cyclohexyltetrazol-5-yl)propoxy]-3,4-dihydrocarbostyril
1-Methyl-6-[3-(1-ethyltetrazol-5-yl)propoxy]carbostyril
1-Ethyl-8-[3-(1-ethyltetrazol-5-yl)propoxy]-3,4-dihydrocarbostyril
1-Methyl-5-[3-(1-cyclohexyltetrazol-5-yl)propoxy]carbostyril
1-Allyl-6-[3-(1-cyclohexyltetrazol-5-yl)propoxy]carbostyril
1-Crotyl-5-[4-(1-cyclohexyltetrazol-5-yl)butoxy]-3,4-dihydrocarbostyril
1-Allyl-7-[3-(1-cyclooctyltetrazol-5-yl)propoxy]carbostyril
1-Allyl-6-[3-(1-ethyltetrazol-5-yl)propoxy]carbostyril
1-Allyl-8-[4-(1-isopropyltetrazol-5-yl)butoxy]carbostyril
1-Acetyl-6-[3-(1-cyclohexyltetrazol-5-yl)propoxy]carbostyril
1-Propionyl-6-[3-(1-cyclohexyltetrazol-5-yl)propoxy]-3,4-dihydroxycarbostyril
1-Acetyl-5-[3-(1-cyclohexyltetrazol-5-yl)propoxy]carbostyril
1-Isobutyryl-8-[3-(1-cyclohexyltetrazol-5-yl)propoxy]-3,4-dihydrocarbostyril
1-Acetyl-6-[3-(1-ethyltetrazol-5-yl)propoxy]carbostyril
1-Acetyl-7-[4-(1-ethyltetrazol-5-yl)butoxy]-3,4-dihydrocarbostyril
1-Benzoyl-6-[3-(1-cyclohexyltetrazol-5-yl)propoxy]carbostyril 1-Benzoyl-5-[3-(1-cyclohexyltetrazol-5-yl)propoxy]carbostyril 1-Benzoyl-7-[3-(1-cyclohexyltetrazol-5-yl)propoxy]-3,4-dihydrocarbostyril 1-Benzoyl-6-[3-(1-ethyltetrazol-5-yl)propoxy]carbostyril 1-Benzyl-6-[3-(1-cyclohexyltetrazol-5-yl)propoxy]carbostyril 1-Benzyl-5-[3-(1-cyclohexyltetrazol-5-yl)propoxy]carbostyril 1-β-Phenethyl-6-[3-(1-cyclohexyltetrazol-5-yl)propoxy]-3,4-dihydrocarbostyril 1-Benzyl-8-[3-(1-cyclohexyltetrazol-5-yl)propoxy]carbostyril 1-Benzyl-6-[3-(1-ethyltetrazol-5-yl)propoxy]carbostyril 1-Benzyl-7-[4-(1-ethyltetrazol-5-yl)butoxy]-3,4-dihydrocarbostyril 6-[2-Methyl-3-(1-cyclohexyltetrazol-5-yl)propoxy]carbostyril 6-[2,2-Dimethyl-3-(1-cyclohexyltetrazol-5-yl)propoxy]carbostyril 6-[1-Methyl-3-(1-cyclooctyltetrazol-5-yl)propoxy]carbostyril 6-[2-Methyl-3-(1-benzyltetrazol-5-yl)propoxy]carbostyril 6-[3-Methyl-4-(1-cyclohexyltetrazol-5-yl)butoxy]carbostyril 6-[2-Ethyl-2-(1-cyclohexyltetrazol-5-yl)ethoxy]carbostyril 6-[3-Methyl-3-(1-cyclohexyltetrazol-5-yl)propoxy]carbostyril 6-[2-Methyl-3-(1-cyclohexyltetrazol-5-yl)propoxy]-3,4-dihydrocarbostyril 6-[2-Methyl-3-(1-benzyltetrazol-5-yl)propoxy]-3,4-dihydrocarbostyril 6-[2,2-Dimethyl-3-(1-cyclohexyltetrazol-5-yl)propoxy]carbostyril 5-[2-Methyl-3-(1-cyclohexyltetrazol-5-yl)propoxy]carbostyril 5-[2-Methyl-3-(1-benzyltetrazol-5-yl)propoxy]carbostyril 1-Methyl-6-[2-methyl-3-(1-cyclohexyltetrazol-5-yl)propoxy]carbostyril 6-[2-Methyl-3-(1-cyclohexylmethyltetrazol-5-yl)propoxy]carbostyril 6-[2-Methyl-3-(1-phenyltetrazol-5-yl)propoxy]carbostyril 1-Benzyl-6-[3-methyl-4-(1-benzyltetrazol-5-yl)butoxy]carbostyril 4-[2-Methyl-3-(1-cyclohexyltetrazol-5-yl)propoxy]carbostyril 8-[3-(1-Isopropyltetrazol-5-yl)propoxy]carbostyril 8-[3-(1-Cyclooctyltetrazol-5-yl)propoxy]-3,4-dihydrocarbostyril 8-[3-(1-Cyclohexyltetrazol-5-yl)propoxy]-3,4-dihydrocarbostyril 8-(1-Cyclohexyltetrazol-5-yl-methoxy)carbostyril 6-[3-(1-Cyclohexylmethyltetrazol-5-yl)propoxy]carbostyril 6-{3-[1-(2-Cyclohexylethyl)tetrazol-5-yl]propoxy}carbostyril 5-[3-(1-Cyclohexylmethyltetrazol-5-yl)propoxy]carbostyril 7-[3-(1-Cyclooctylmethyltetrazol-5-yl)propoxy]carbostyril 6-[3-(1-Cyclohexylmethyltetrazol-5-yl)propoxy]-3,4-dihydrocarbostyril 1-Methyl-6-[3-(1-cyclohexylmethyltetrazol-5-yl)propoxy]carbostyril 1-Allyl-5-[3-(1-cyclohexylmethyltetrazol-5-yl)propoxy]-3,4-dihydrocarbostyril 1-Benzyl-6-[3-(1-cyclohexylmethyltetrazol-5-yl)propoxy]carbostyril 1-Acetyl-6-[3-(1-cyclohexylmethyltetrazol-5-yl)propoxy]carbostyril 6-[3-(1-Phenyltetrazol-5-yl)propoxy]carbostyril 6-[3-(1-Phenyltetrazol-5-yl)propoxy]-3,4-dihydrocarbostyril 5-[3-(1-Phenyltetrazol-5-yl)propoxy]carbostyril 4-[3-(1-Phenyltetrazol-5-yl)propoxy]carbostyril 8-[3-(1-Phenyltetrazol-5-yl)propoxy]-3,4-dihydrocarbostyril 1-Methyl-6-[3-(1-phenyltetrazol-5-yl)propoxy]carbostyril 1-Acetyl-6-[3-(1-phenyltetrazol-5-yl)propoxy]carbostyril 1-Benzyl-6-[3-(1-phenyltetrazol-5-yl)propoxy]carbostyril 1-Allyl-5-[3-(1-phenyltetrazol-5-yl)propoxy]-3,4-dihydrocarbostyril 7-(1-Benzyltetrazol-5-yl-methoxy)-3,4-dihydrocarbostyril 6-[3-(1-Benzyltetrazol-5-yl)propoxy]carbostyril 6-[3-(1-β-Phenethyltetrazol-5-yl)propoxy]carbostyril 6-[3-(1-Benzyltetrazol-5-yl)propoxy]-3,4-dihydrocarbostyril 5-[3-(1-Benzyltetrazol-5-yl)propoxy]carbostyril 7-[3-(1-Benzyltetrazol-5-yl)propoxy]-3,4-dihydrocarbostyril 8-[3-(1-Benzyltetrazol-5-yl)propoxy]-3,4-dihydrocarbostyril 1-Methyl-6-[3-(1-benzyltetrazol-5-yl)propoxy]carbostyril 1-Allyl-5-[3-(1-benzyltetrazol-5-yl)propoxy]-3,4-dihydrocarbostyril 1-Benzyl-6-[3-(1-benzyltetrazol-5-yl)propoxy]carbostyril 1-Acetyl-6-[3-(1-benzyltetrazol-5-yl)propoxy]carbostyril 1-Benzyl-6-[3-(1-benzyltetrazol-5-yl)propoxy]carbostyril 6-{3-[1-(4-Phenylbutyl)tetrazol-5-yl]propoxy}carbostyril 6-[3-(1-Cyclohexyltetrazol-5-yl)propoxy]-4-ethylcarbostyril 6-[3-(1-Cyclohexyltetrazol-5-yl)propoxy]-1,4-dimethylcarbostyril 5-[3-(1-Benzyltetrazol-5-yl)propoxy]-4-methylcarbostyril 6-[3-(1-Ethyltetrazol-5-yl)propoxy]-4-methylcarbostyril 7-[3-(1-Phenyltetrazol-5-yl)propoxy]-4-methylcarbostyril 1-(3,4,5-Trimethoxybenzoyl)-6-[3-(1-cyclohexylmethyltetrazol-5-yl)propoxy]-3,4-dihydrocarbostyril 1-(3,4-Dimethoxybenzoyl)-6-[3-(1-cyclohexyltetrazol-5-yl)propoxy]-3,4-dihydrocarbostyril 1-(4-Chlorobenzoyl)-6-[3-(1-benzyltetrazol-5-yl)propoxy]-3,4-dihydrocarbostyril 1-(2-Methylbenzoyl)-5-[3-(1-cyclohexyltetrazol-5-yl)propoxy]carbostyril 1-(4-Chlorobenzyl)-6-[3-(1-cyclohexyltetrazol-5-yl)propoxy]carbostyril 1-(β-3,4-Dimethoxyphenethyl)-6-[3-(1-benzyltetrazol-5-yl)propoxy]carbostyril 1-(2-Methylbenzyl)-6-[3-(1-cyclohexyltetrazol-5-yl)propoxy]-3,4-dihydrocarbostyril 1-(β-3,4-Methylenedioxyphenethyl)-6-[4-(1-cyclohexyltetrazol-5-yl)butoxy]carbostyril 6-{3-[1-(4-Chlorobenzyl)tetrazol-5-yl]propoxy}carbostyril 6-{3-[1-(3,5-Dichlorobenzyl)tetrazol-5-yl]propoxy}carbostyril 5-{3-[1-(β-2-Bromophenethyl)tetrazol-5-yl]propoxy}carbostyril 6-{3-[1-(4-Methoxybenzyl)tetrazol-5-yl]propoxy}carbostyril 6-{3-[1-(β-3,4-Dimethoxyphenethyl)tetrazol-5-yl]propoxy}carbostyril 5-{3-[1-(β-3,4-Dimethoxyphenethyl)tetrazol-5-yl]propoxy}carbostyril 6-{3-[1-(2-Methylbenzyl)tetrazol-5-yl]propoxy}carbostyril 6-{3-[1-(β-3,4-Dimethylphenethyl)tetrazol-5-yl]propoxy}carbostyril 6-{3-[1-(β-3,4-Methylenedioxyphenethyl)tetrazol-5-yl]propoxy}carbostyril 6-{3-[1-(β-4-Dimethylaminophenethyl)tetrazol-5-yl]propoxy}carbostyril 6-{3-[1-(4-Chlorophenyl)tetrazol-5-yl]propoxy}carbostyril 5-{3-[1-(3,5-Dichlorophenyl)tetrazol-5-yl]propoxy}carbostyril 6-{3-[1-(4-Methoxyphenyl)tetrazol-5-yl]propoxy}carbostyril 6-{3-[1-(2-Methylphenyl)tetrazol-5-yl]propoxy}carbostyril 6-[1-(4-Ethylphenyl)tetrazol-5-yl-methoxy]3,4-dihydrocarbostyril 6-{4-[1-(3,4-Dimethylphenyl)tetrazol-5-yl]butoxy}carbostyril 6-{3-[1-(3,4-Methylenedioxyphenyl)tetrazol-5-yl]propoxy}carbostyril 6-[1-(2-Chloro-4-nitrophenyl)tetrazol-5-yl-methoxy]-3,4-dihydrocarbostyril 5-{3-[1-(4-Dimethylaminophenyl)tetrazol-5-yl]propoxy}carbostyril 4-Methyl-7-[3-(1-cyclohexyltetrazol-5-yl)propoxy]carbostyril 7-[3-(1-Phenyltetrazol-5-yl)propoxy]-3,4-dihydrocarbostyril 1-Ethyl-6-[3-(1-cyclohexylmethyltetrazol-5-yl)propoxy]-3,4-dihydrocarbostyril 1-Propionyl-6-(1-benzyltetrazol-5-yl-methoxy)-3,4-dihydrocarbostyril 6-[4-(1-Cyclohexyltetrazol-5-yl)butoxy]carbostyril 6-[3-(1-Cyclooctyltetrazol-5-yl)propoxy]carbostyril 6-(1-Benzyltetrazol-5-yl-methoxy)carbostyril 5-[3-(1-Cyclopentyltetrazol-5-yl)propoxy]-3,4-dihydrocarbostyril 1-Benzoyl-5-(1-cyclohexyltetrazol-5-yl-methoxy)-3,4-dihydrocarbostyril 4-[3-(1-Cyclohexylmethyltetrazol-5-yl)propoxy]carbostyril The compounds of the present invention can be prepared according to various processes such as that expressed by the following reaction process formula-1:

Reaction process formula-1

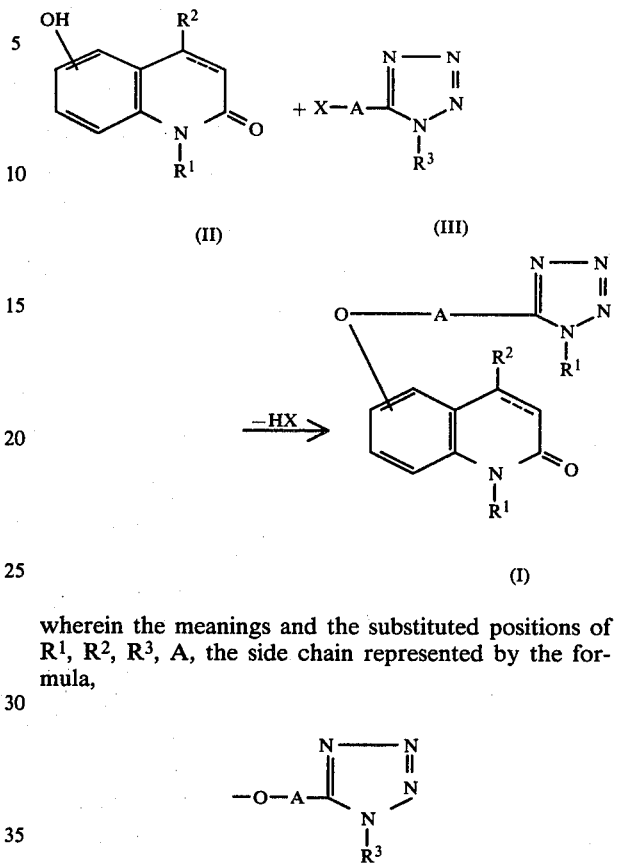

wherein the meanings and the substituted positions of $R^1$, $R^2$, $R^3$, A, the side chain represented by the formula, $$-O-A-\underset{\underset{R^3}{|}}{\overset{N---N}{\underset{N}{\overset{\|}{\diagdown}}}}N$$

and the carbon-carbon bond between 3- and 4-positions of the carbostyril skeleton are all same as defined above; X is a halogen atom; and the substituted position of —OH is any one at 4-, 5-, 6-, 7- or 8-position of the carbostyril skeleton.

As can be seen from the reaction process formula-1 that, tetrazolylalkoxycarbostyril derivative (I) of the present invention can be prepared by reacting a hydroxycarbostyril derivative (II) with a tetrazol derivative (III) under a conventional dehydrohalogenation reaction. As to the halogen atom in the formula (III), bromine, chlorine or iodine atom can be exemplified. The dehydrohalogenation reaction is carried out by using a basic compound as dehydrohalogenating agent. Said basic compound used in the reaction may be selected from a wide variety of known basic compounds including inorganic bases such as sodium hydroxide, potassium hydroxide, sodium carbonate, potassium carbonate, sodium hydrogencarbonate, potassium hydrogencarbonate or silver carbonate; alkali metals such as sodium or potassium; alkolates such as sodium methylate or sodium ethylate; organic bases such as triethylamine, pyridine, N,N-dimethylaniline, N-methylmorpholine, 4-dimethylaminopyridine, 1,5-diaza-bicyclo[4,3,0]-nonene-5 (DBN), 1,5-diaza-bicyclo[5,4,0]-undecene-5-(DBU), or 1,4-diaza-bicyclo[2,2,2]-octane (DABCO). The above reaction can be carried out in the absence or presence of a solvent. The solvent used in this reaction may be of any known inert type which gives no adverse effect to the reaction. Among the examples of the solvents are alcohols such as methanol, ethanol, propanol, butanol, ethyleneglycol, etc.; ethers such as dimethyl ether, tetrahydrofuran, dioxane, monoglyme or diglyme, etc.; ketones such as acetone, methylethylketone, etc.; aromatic hydrocarbons such as benzene, toluene, xylene, etc.; esters such as methylacetate, ethylacetate, etc.; and aprotic polar solvents such as N,N-dimethylformamide, dimethylsulfoxide, hexamethylphosphoryl trimaide, etc. It is advantageous to carry out the said reaction in the presence of a metallic iodide such as sodium iodide or potassium iodide.

The ratio of amount of hydroxycarbostyril derivative (II) to tetrazol derivative (III) in the above method is not subjected to any specific restriction and may be suitably selected from a wide range, and usually, it is desirable that the latter is used in equimolar to 5 times the molar quantity, preferably equimolar to double the molar quantity of the former. The reaction temperature is also not subjected to any particular definition, and the reaction is usually carried out at a room temperature to 200° C., preferably at 50° to 150° C. The reaction time is usually 1 to 30 hours, preferably 1 to 15 hours.

The hydroxycarbostyril derivative (II) used as one of the starting materials in the above method is known compound, but the tetrazol derivative (III) used as another part of the starting materials is novel compound and is prepared by a method such as the following reaction process formula-2:

Reaction process formula-2

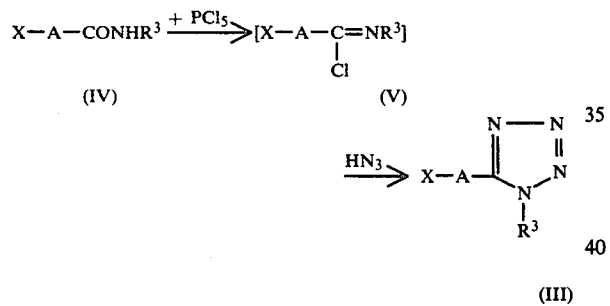

(IV)  (V)

(III)

wherein X is a halogen atom such as chlorine, bromine or iodine atom; $R^3$ and A are all same as defined above.

Thus, the tetrazol derivative (III) can be prepared by reacting a haloamide derivative represented by the general formula (IV) with phosphorus pentachloride (PCl$_5$) to obtain a haloimine derivative (V) according to a known method or a method similar to a known method, then without separating, the haloimine derivative (V) is reacted with hydrogen azide (HN$_3$). Generally, the reaction of haloamide (IV) with phosphorus pentachloride is carried out in the presence of a solvent. The solvent used in this reaction may be of any known inert type which gives no adverse effect to the reaction. Among the examples of such solvent are aromatic hydrocarbons such as benzene, xylene, toluene, etc.; halogenated aromatic hydrocarbons such as chlorobenzenes, bromobenzenes, etc.; ethers such as diethyl ether, dioxane, etc.; aliphatic hydrocarbons such as n-hexane, n-heptane, etc. The ratio of amount of haloamide (IV) to phosphorus pentachloride in the above reaction is usually selected from a wide range, and it is desirable that the latter is used in an equimolar to 2 times the molar quantity, preferably an equimolar to 1.2 times the molar quantity of the former. The reaction is usually carried out at −20° to 50° C., preferably at 0° to 25° C.

The reaction time is usually 30 minutes to 5 hours, preferably, 1 to 3 hours.

Without being separated from the reaction system, the thus obtained haloimine derivative (V) is then reacted with hydrogen azide (HN$_3$) (usually used as in the form of a solution of benzene, xylene, diethyl ether, n-hexane, etc.). The ratio of amount of haloimine derivative (V) to hydrogen azide (HN$_3$) is usually selected so that the latter is used in equimolar to 5 times the molar quantity, preferably, equimolar to 3 times the molar quantity of the former. The reaction is carried out at 0° to 150° C. and the reaction time is 8 hours to 2 days.

The compounds of the present invention can also be prepared by methods according to the following reaction process formulas-3 and -4:

Reaction process formula-3:

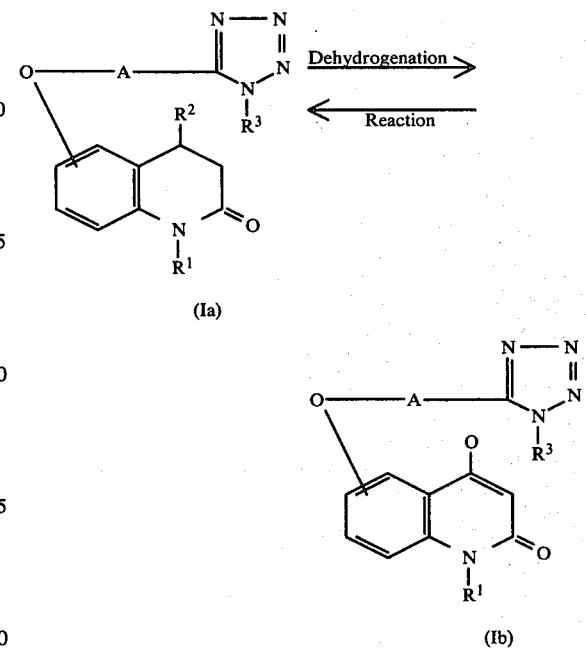

Reaction process formula-4:

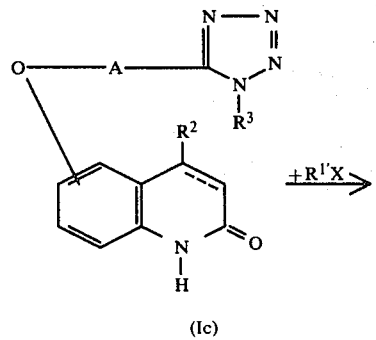

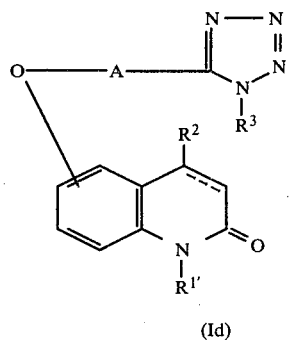

(Id)

wherein $R^{1'}$ is a lower alkyl, a lower alkenyl, a lower alkanoyl, a benzoyl or a phenylalkyl group; $R^1$, $R^2$, $R^3$, X, A, the carbon-carbon bond between 3- and 4-positions in the carbostyril skeleton and the substituted positions of the each of the substituted groups are all same as defined above.

Thus, a compound of the general formula (Ib) can be obtained by dehydrogenating a compound of the general formula (Ia), while a compound of the general formula (Ia) can be obtained by reducing a compound of the general formula (Ib). Furthermore, a compound of the general formula (Id) can be produced from a dehydrohalogenation reaction of a compound of the general formula (Ic) with a compound of the general formula (VI).

In reaction process formula-3, the dehydrogenation of a compound of the general formula (Ia) can be accomplished according to a usual method by subjecting the compound to a dehydrogenation reaction in a suitable solvent by using an oxidizing agent. As to the oxidizing agents which may be used in this reaction are, for example, benzoquinones such as 2,3-dichloro-5,6-dicyanobenzoquinone (hereinafter referred to as DDQ), chloranil (2,3,5,6-tetrachlorobenzoquinone), etc.; metallic catalysts such as selenium dioxide, palladium carbon, etc.; and brominating agents such as N-bromosuccinimide, bromine, etc. As to the solvents which may be used in this reaction are, ethers such as dioxane, tetrahydrofuran, 2-methoxyethanol, dimethoxyethane, etc.; aromatic hydrocarbons such as benzene, toluene, xylene, etc.; halogenated hydrocarbons such as dichloromethane, dichloroethane, chloroform, carbon tetrachloride, etc.; alcohols such as butanol, amyl alcohol, hexanol, etc., and aprotic polar solvents such as N,N-dimethylformamide, dimethylsulfoxide, hexamethylphosphoryl triamide, etc. This reaction is usually carried out at a temperature within the range of room temperature to 300° C., preferably 50° to 200° C., for a period of 1 hour to 2 days, preferably 1 to 20 hours. In case of using a benzoquinone or brominating agent as the oxiding agent, it is usually used in an amount of 1 to 5 times, preferably 1 to 2 times the moles of compound (Ia).

In the reaction process formula-3, the catalytic reduction of the compound (Ib) can be accomplished in a usual way by hydrogenating said compound in a suitable solvent by using a catalyst. Any known type of catalysts may be used for this reduction reaction. As examples thereof, one may cite platinum catalysts such as platinum wire, platinum plate, platinum sponge, platinum black, platinum oxide, colloidal platinum, etc.; palladium catalysts such as palladium sponge, palladium black, palladium oxide, palladium-barium sulfate, palladium-barium carbonate, palladium carbon, palladium silica gel, colloidal palladium, etc.; platinum group catalysts such as asbestos-filled rhodium, iridium, colloidal rhodium, ruthenium catalysts, colloidial iridium, etc., nickel catalysts such as reduced nickel, nickel oxide, Raney nickel, Urushibara nickel, nickel catalysts produced from thermal decomposition of nickel formate, nickel boride, etc.; cobalt catalysts such as reduced cobalt, Raney cobalt, Urushibara cobalt, etc.; iron catalysts such as reduced iron, Raney iron, etc.; copper catalysts such as reduced copper, Raney copper, Ullmann copper, etc.; and other metallic catalysts such as zinc. The solvent used in the above reaction may be, for example, a lower alcohol (such as methanol, ethanol, isopropanol, etc.), water, acetic acid, an acetic acid ester (such as methyl acetate, ethyl acetate, etc.), ethylene glycol, an ether (such as diethyl ether, tetrahydrofuran, dioxane, etc.), an aromatic hydrocarbon (such as benzene, toluene, xylene, etc.), a cycloalkane (such as cyclopentane, cyclohexane, etc.), an n-alkane (such as n-hexane, n-pentane, etc.). The reaction is carried out under normal hydrogen pressure or under pressure, preferably under 1 to 20 atm., and at a temperature between room temperature and the boiling point of the solvent, preferably between room temperature and 100° C.

In the reaction process formula-4, the reaction between the compound (Ic) and the compound (VI) is carried out by reacting the compound (Ic) in the form of an alkali metal salt with the compound (VI). The reaction for obtaining an alkali metal salt from the compound (Ic) is conducted in the presence of an alkali metal compound. The alkali metal compound used here may be, for example, a metallic hydride such as sodium hydride, potassium hydride, etc.; an alkali metal such as metallic sodium, or sodium azide. This reaction is usually carried out in a solvent. Among the solvents usable in this reaction are aromatic hydrocarbon solvents such as benzene, toluene, xylene, etc.; ether solvents such as diethyl ether, 1,2-dimethoxyethylene, dioxane, etc.; and aprotic polar solvents such as dimethylformamide, dimethylsulfoxide, hexamethylphosphoryl triamide, etc.; among these solvents, the last-said aprotic polar solvents are most preferable. The alkali metal compound is usually used in an amount of 1 to 5 times, preferably 1 to 3 times the molar quantity of the compound (Ic). The reaction temperature may be suitably selected from a wide range, usually 0° to 200° C., and the reaction advances most advantageously within the range of room temperature to 50° C. This reaction provides a compound (Ic) where the nitrogen atom at the 1-position has been substituted with an alkali metal. The reaction for obtaining the compound (Id) from an alkali metal salt of the above-obtained compound (Ic) with the compound (VI) is a condensation reaction. This condensation reaction may be accomplished easily in a usual way, but generally this reaction advances in a most preferred mode by reacting both compounds at room temperature in a solvent, for example, dimethylformamide. The amount of the compound (VI) used may be suitably selected from a wide range, but usually it is desirably used in an amount of 1 to 5 times the molar quantity, most preferably 1 to 3 times the molar quantity of the alkali metal salt of the compound (Ic).

The process of the present invention is not limited to the above-described two-stage operation; it is of course possible to carry out the reaction by introducing the three compounds, that is, the compounds of the general formulae (Ic) and (VI) and said alkali metal compound simultaneously into the reaction system, and in this case, too, it is possible to obtain the compound (Id) of the present invention through the same course of reaction as said above.

The thus obtained compound (I) of the present invention can be easily isolated and refined by usual separation means such as solvent extraction, solvent dilution, recrystallization, and column chromatography with liquid.

The compounds of the present invention can be administered, either in the form as they are or together with a pharmaceutically acceptable carrier, to animals as well as to human being. No particular restriction is placed on the administration unit forms and the compounds can be used in any desired unit form. Suitable administration unit forms include such oral administration forms as tablets, capsules, granules, etc.; and parenteral administration forms such ss injections. The dosage of the active ingredient to be administered is not subjected to any particular definition and admits of selection from a wide range, but in order to obtain a desired pharmacological effect, it is recommended to select said dosage from the range of 0.06 to 10 mg per kg body weight per day. It is also suggested to contain 1 to 500 mg of the active ingredient in each unit dose of the administration forms.

The compounds of the present invention can be formed into the desired peroral preparations such as tablets, capsules, solutions, etc., according to a common method. For preparation of tablets, a compound of the present invention is mixed with a pharmaceutically acceptable excipient such as gelatin, starch, lactose, magnesium stearate, talc, gum arabic or the like and shaped into tablets. Capsules can be obtained by mixing a compound of this invention with an inert pharmaceutically acceptable filler or diluent and filling the mixture into rigid gelatin capsules or soft capsules. Sirup or elixir may be prepared by mixing a compound of the present invention with a sweetening such as sucrose, antiseptic such as methyl- and propyl-parabens, colorant, seasoning and/or other suitable additives.

Parenteral preparations can be also obtained according to a common method. In this case, the compound of the present invention is dissolved in a sterilized liquid vehicle. The preferred vehicle is water or saline water. Liquid preparations having desired transparency, stability and parenteral use adaptability can be obtained by dissolving approximately 1 to 500 mg of the active ingredient in a solution of polyethylene glycol (having molecular weight of 200 to 5000) which is soluble in both water and organic solvents. Desirably, such liquid preparations contain a lubricant such as sodium carboxymethyl cellulose, methyl cellulose, polyvinyl pyrrolidone, polyvinyl alcohol or the like. Said liquid preparations may also contain a bactericide and fungicide such as benzyl alcohol, phenol or thimerosal and, if necessary, an isotonic agent such as sucrose or sodium chloride, a local anesthetic, stabilizer, buffer, etc. For additional ensurance of stability, the parenteral compositions may be frozen after filling and dehydrated by the known freeze-drying techniques. The freeze-dried powder can be returned to the normal use form just before use.

PREPARATION OF TABLES 1,000 Tablets for peroral use, each containing 5 mg of 6-[3-(1-cyclohexyltetrazol-5-yl)propoxy]carbostyril, are prepared from the following prescription.

| Ingredient | Amount (g) |
| --- | --- |
| 6[3-(1-Cyclohexyltetrazol-5-yl)-propoxy]carbostyril | 5 |
| Lactose (J.P. = Japanese Pharmacopoeia) | 50 |
| Corn starch (J.P.) | 25 |
| Crystalline cellulose (J.P.) | 25 |
| Methyl cellulose (J.P.) | 1.5 |
| Magnesium stearate (J.P.) | 1 |

The above specified 6-[3-(1-cyclohexyltetrazol-5-yl)propoxy]carbostyril, lactose, corn starch and crystalline cellulose are mixed well, and the mixture is added with a 5% aqueous solution of methyl cellulose and then granulated. The obtained granules are passed through a 200 mesh sieve and then dried carefully. The dried granules passed through a 200 mesh sieve are admixed with magnesium stearate, and then compressed into tablets.

PREPARATION OF CAPSULES 1,000 Pieces of two-piece rigid gelation capsules for peroral use, each containing 10 mg of 6-[3-(1-cyclohexyltetrazol-5-yl)propoxy]carbostyril, are prepared from the following prescription.

| Ingredient | Amount (g) |
| --- | --- |
| 6-[3-(1-Cyclohexyltetrazol-5-yl)-propoxy]carbostyril | 10 |
| Lactose (J.P.) | 80 |
| Starch (J.P.) | 30 |
| Talc (J.P.) | 5 |
| Magnesium stearate (J.P.) | 1 |

The above components are finely ground, then stirred and mixed sufficiently to form a uniform mixture and then filled into the gelatin capsules with a size convenient for peroral administration.

PREPARATION OF INJECTIONS

A sterile aqueous solution suitable for parenteral use is prepared from the following prescription.

| Ingredient | Amount (g) |
| --- | --- |
| 6-[3-(1-Cyclohexyltetrazol-5-yl)-propoxy]carbostyril | 1 |
| Polyethylene glycol (J.P.), [molecular weight: 4,000] | 0.3 |
| Sodium chloride (J.P.) | 0.9 |
| Polyoxyethylene sorbitan mono-oleate (J.P.) | 0.4 |
| Sodium metabisulfite | 0.1 |
| Methyl p-hydroxybenzoate (J.P.) | 0.18 |
| Propyl p-hydroxybenzoate (J.P.) | 0.02 |
| Distilled water for injection | 100 ml |

A mixture of the above-prescribed methyl p-hydroxybenzoate, propyl p-hydroxybenzoate, sodium metabisulfite and sodium chloride, while stirred, is dissolved in about half the quantity of distilled water at 80° C. The obtained solution is cooled to 40° C., and then 6-[3-(1-cyclohexyltetrazol-5-yl)propoxy]carbostyril, polyethylene glycol and polyoxyethylene sorbitan monooleate are dissolved in that order in said solution. This solution is further added with distilled water for injection to the final regulated volume and then sterilized by sterile filtration with a suitable filter paper.

The results of the pharmacological tests on the compounds of this invention are shown below.

PHARMACOLOGICAL TEST 1

(Test of platelet aggregation inhibitory effect)

The platelet aggregation inhibitory effect is measured by using AG-II Aggregometer (manufactured by Bryston Manufacturing Co.) according to a method similar to that disclosed in G. R. Born: [Nature, 927–929 (1962)]. The blood sample used for the test is a 1/9 (by volume) mixture of sodium citrate and whole blood collected from rabbit. Said sample is subjected to 10-minute centrifugal separation at 1,000 r.p.m. to obtain a platelet rich plasma (PRP). The thus obtained PRP is separated, and the remaining blood sample is further subjected to 15-minute centrifugal separation at 3,000 r.p.m. to obtain a platelet poor plasma (PPP).

The number of platelets in the PRP is counted by the Brecher-Clonkite Method, and the PRP is diluted with the PPP to prepare a PRP sample with platelet concentration of 300,000/mm$^3$ for the adenosine diphosphate (ADP)-induced aggregation test. There is also prepared a PRP sample with platelet concentration of 450,000/mm$^3$ for the collagen-induced aggregation test.

0.6 Ml of said PRP sample is added into 0.01 ml of a solution of a test compound of a predetermined concentration and the mixture is placed in a 37° C. thermostat for one minute. Then 0.07 ml of an ADP or collagen solution is added to the mixture. Transmittance of this mixture is determined and the change of transmittance is recorded by using the aggregometer at stirrer speed of 1,100 r.p.m. In this test, Auren Beronal buffer (pH 7.35) is used for the preparation of the ADP or collagen solution. ADP is adjusted to a concentration of $7.5 \times 10^{-5}$ M, and the collagen solution is prepared by triturating 100 mg of collagen with 5 ml of said buffer and the supernatant is used as collagen inducer. Adenosine and acetylsalicylic acid are used as controls for the ADP-induced aggregation test and the collagen-induced aggregation test, respectively. The platelet aggregation inhibitory effect is measured in terms of percent inhibition with respect to the aggregation rate of the controls. The aggregation rate is calculated from the following formula:

$$\text{Aggregation rate} = \frac{c - a}{b - a} \times 100$$

wherein
a: transmittance of PRP
b: transmittance of PRP containing a test compound and an aggregation inducer
c: transmittance of PPP.

The inhibitory effect of the test compounds on collagen-induced aggregation in rabbit platelets is shown in Table 1, and such effect on ADP-induced aggregation is shown in Table 2. The compounds tested are as follows.

TEST COMPOUNDS

No. Compounds of the present invention (Nos. 1–16)

1. 6-[3-(1-Cyclohexyltetrazol-5-yl)propoxy]-carbostyril
2. 6-[3-(1-Isopropyltetrazol-5-yl)propoxy]-carbostyril
3. 6-[3-(1-Cyclohexyltetrazol-5-yl)propoxy]-3,4-dihydrocarbostyril
4. 6-[3-(1-Benzyltetrazol-5-yl)propoxy]-carbostyril
5. 6-[3-(1-Cyclohexylmethyltetrazol-5-yl)-propoxy]carbostyril
6. 6-[3-(1-Cyclooctyltetrazol-5-yl)propoxy]-carbostyril
7. 6-[4-(1-Cyclohexyltetrazol-5-yl)propoxy]-carbostyril
8. 1-Methyl-6-[3-(1-cyclohexyltetrazol-5-yl)-propoxy]carbostyril
9. 6-[3-(1-Phenyltetrazol-5-yl)propoxy]carbostyril
10. 4-Methyl-6-[3-(1-cyclohexyltetrazol-5-yl)propoxy]-carbostyril
11. 5-[3-(1-Cyclohexyltetrazol-5-yl)propoxy]-3,4-dihydrocarbostyril
12. 1-Benzyl-6-[3-(1-cyclohexyltetrazol-5-yl)propoxy]-carbostyril
13. 1-Allyl-6-[3-(1-cyclohexyltetrazol-5-yl)propoxy]-carbostyril
14. 1-Acetyl-6-[3-(1-cyclohexyltetrazol-5-yl)propoxy]-3,4-dihydrocarbostyril
15. 6-[1-(4-Ethylphenyltetrazol-5-yl)methoxy]-3,4-dihydrocarbostyril
16. 1-(3,4,5-Trimethoxybenzoyl)-6-[3-(1-cyclohexyl-tetrazol-5-yl)propoxy]-3,4-dihydrocarbostyril Known compounds (comparative compounds) (Nos. 17–26)

17. Aspirin (reference compound)
18. 6-[3-(5-Methylthiotetrazol-1-yl)propoxy]-3,4-dihydrocarbostyril
19. 6-[3-(5-Methylthiotetrazol-2-yl)propoxy]-3,4-dihydrocarbostyril
20. 6-[3-(Tetrazol-1-yl)propoxy]-3,4-dihydrocarbostyril
21. 5-(2-Piperidinoethoxy)-3,4-dihydrocarbostyril
22. 5-(2-Morpholinoethoxy)-3,4-dihydrocarbostyril
23. 5-(3-Piperidinopropoxy)-3,4-dihydrocarbostyril
24. 6-(2-Morpholinoethoxy)-3,4-dihydrocarbostyril
25. 7-(3-Piperidinopropoxy)-3,4-dihydrocarbostyril
26. 8-(2-Piperidinopropoxy)-3,4-dihydrocarbostyril

TABLE 1

Inhibition effect of carbostyril derivatives on collagen-induced aggregation in rabbit platelet

| | Test compound No. | Concentration of the test compound solution | | |
|---|---|---|---|---|
| | | $10^{-4}$ mole % | $10^{-5}$ mole % | $10^{-6}$ mole % |
| Compounds of the present invention | 1 | 100.0 | 100.0 | 25.9 |
| | 2 | 100.0 | 58.1 | 11.8 |
| | 3 | 100.0 | 53.5 | 10.3 |
| | 4 | 100.0 | 72.5 | 10.8 |
| | 5 | 100.0 | 100.0 | 24.7 |
| | 6 | 100.0 | 100.0 | 27.4 |
| | 7 | 100.0 | 100.0 | 26.8 |
| | 8 | 91.5 | 43.4 | 18.6 |
| | 9 | 100.0 | 100.0 | 32.8 |
| | 10 | 100.0 | 100.0 | 18.2 |
| | 11 | 98.4 | 42.4 | — |
| | 12 | 92.6 | 41.5 | 21.8 |
| | 13 | 89.7 | 44.8 | 23.2 |
| | 14 | 86.8 | 47.3 | — |
| | 15 | 100.0 | 35.1 | — |
| | 16 | 91.3 | 45.3 | — |
| Known compounds (Reference compounds) | 17 | 65 | 9 | 7 |
| | 18 | 67.4 | 13.3 | — |
| | 19 | 73.4 | 1.3 | — |
| | 20 | 77.4 | 0 | — |
| | 21 | 25 | — | — |
| | 22 | 23 | — | — |
| | 23 | 27 | — | — |
| | 24 | 31 | — | — |

TABLE 1-continued

Inhibition effect of carbostyril derivatives on collagen-induced aggregation in rabbit platelet

| Test compound No. | Concentration of the test compound solution | | |
|---|---|---|---|
| | $10^{-4}$ mole % | $10^{-5}$ mole % | $10^{-6}$ mole % |
| 25 | 18 | — | — |
| 26 | 12 | — | — |

TABLE 2

Inhibition effect of carbostyril derivatives on ADP-induced aggregation in rabbit platelet

| | Test compound No. | Concentration of the test compound solution | | |
|---|---|---|---|---|
| | | $10^{-4}$ mole % | $10^{-5}$ mole % | $10^{-6}$ mole % |
| Compounds of the present invention | 1 | 100.0 | 63.4 | 32.7 |
| | 2 | 74.7 | 36.8 | 11.9 |
| | 3 | 76.7 | 59.6 | 9.6 |
| | 4 | 100.0 | 45.5 | 3.7 |
| | 5 | 100.0 | 64.1 | 34.2 |
| | 6 | 100.0 | 75.5 | 30.5 |
| | 7 | 100.0 | 59.9 | 28.7 |
| | 8 | 87.8 | 42.4 | 21.3 |
| | 9 | 100.0 | 45.1 | 26.8 |
| | 10 | 100.0 | 61.7 | 28.1 |
| | 11 | 90.4 | 30.2 | — |
| | 12 | 76.8 | 35.2 | — |
| | 13 | 81.6 | 41.7 | — |
| | 14 | 79.4 | 43.2 | — |
| | 15 | 78.5 | 38.9 | — |
| | 16 | 75.6 | 48.4 | — |
| | 17 | 7 | 0 | — |
| | 18 | 0 | — | — |
| Known compounds (Reference compounds) | 19 | 2.3 | — | — |
| | 20 | 4.3 | — | — |
| | 21 | 18 | — | — |
| | 22 | 13 | — | — |
| | 23 | 15 | — | — |
| | 24 | 17 | — | — |
| | 25 | 12 | — | — |
| | 26 | 14 | — | — |

PHARMACOLOGICAL TEST 2

(Test of obstructive action against cyclic AMP phosphodiesterase)

The obstructive action against cyclic AMP phosphodiesterase was measured according to the activity measuring method described in "Biochimica et Biophysica Acta", Vol. 429, pp. 485–497 (1976) and "Biochemical Medicine", Vol. 10, pp. 301–311 (1974).

That is, for determining the obstructive activity against cyclic AMP phosphodiesterase, 10 ml of a solution obtained by adding 1 mmol of $MgCl_2$ into 50 mmol of tris-hydrochloric acid buffer with pH 7.4 was added to the platelets obtained by further centrifuging the above-said rabbit PRP at 3,000 r.p.m. for 10 minutes, and the suspended platelets were ground by a Teflon potter type homogenizer. This was followed by two times of freezing and thawing treatment and 300-second fracturing with 200 watt supersonic waves. After additional 60-minute centrifugation with 100,000 g, the supernatant was collected to use it as a crude enzyme solution.

10 Milliliters of this crude buffer solution was added to a 1.5×20 cm DEAE-cellulose column which has previously been buffered with 50 mmol of tris-acetate buffer (pH 6.0), followed by washing and elution with 30 ml of 50 mmol tris-acetate buffer, and this buffer solution was subjected to linear gradient elution with 0 to 1 moles of sodium acetate-tris-acetate buffer. The flow rate was 0.5 ml/min, and 5 ml of each fraction was batched out. This operation gave a fraction which has low activity of less than 2 n mole/ml/min with high (100 μmole) cyclic AMP substrate concentration and still has high activity of over 100 p moles/ml/min with low (0.4 μmole) cyclic AMP substrate concentration. This fraction was used as cyclic AMP phosphodiesterase.

0.1 Milliliter of an aqueous solution of each test compound of a specified concentration was mixed with 40 mmol of tris-hydrochloric acid buffer (pH 8.0, containing 50 μg of cow serum albumin and 4 mmol of $MgCl_2$) containing predetermined 0.4 μmol of cyclic AMP (tritium cyclic AMP), and 0.2 ml of this mixed solution was used as a substrate solution.

0.2 Milliliter of the above-prepared cyclic AMP phosphodiesterase of a predetermined concentration was added to said substrate solution and the mixture was reacted at 30° C. for 20 minutes, producing tritium 5'-AMP from the tritium cyclic AMP.

The reaction system was then immersed in boiling water for 2 minutes to stop the reaction, and then this reaction solution was cooled in ice water and, for converting the produced tritium 5'-AMP into tritium adenosine, the solution was added with 0.05 ml (1 mg/ml) of snake poison as 5'-nucleotidase and reacted at 30° C. for 10 minutes. The whole amount of this reaction solutions was then added to a cation exchange resin (AG 500 W×4, 200–400 meshes, manufactured by Bio-Rad Co., column size: 0.5×1.5 cm), and the produced tritium anodesine alone was allowed to combine, washed with 6 ml of distilled water and eluted with 1.5 ml of 3 N-ammonia water. The whole quantity of the elutant was added with 10 ml of a triton-toluene type scintillator and the produced tritium adenosine was measured by a liquid scintillation counter to determine the phosphodiesterase activity.

In this way, the phosphodiesterase activation value (Vs) of the test compounds of the respective concentrations was determined, and the phosphodiesterase obstruction rate (%) was determined from said activation value (Vs) and control value (Vc) (obtained from water not containing any test compound) from the following formula:

$$\text{Phosphodiesterase obstruction rate (\%)} = \frac{Vc - Vs}{Vc} \times 100$$

Known papaverine and 1-methyl-3-isobutylxanthine were used as controls. The results are shown in Table 3.

TABLE 3

Phosphodiesterase obstruction rate (%)

| Test Compound No. | Concentration of test compound solution | | | |
|---|---|---|---|---|
| | $10^{-6}$ mole | $10^{-7}$ mole | $10^{-8}$ mole | $10^{-9}$ mole |
| 1 | 92.9 | 83.8 | 58.4 | 44.7 |
| 5 | 89.9 | 73.4 | 55.2 | 38.6 |
| 6 | 88.4 | 79.6 | 57.4 | 36.5 |
| 7 | — | 98.4 | 68.3 | 50.6 |
| Papaverine | 82.4 | 54.6 | 7.2 | — |
| 1-Methyl-3-isobutyl- | 63.4 | 4.2 | — | — |

TABLE 3-continued

| Test Compound No. | Phosphodiesterase obstruction rate (%) Concentration of test compound solution | | | |
|---|---|---|---|---|
| | $10^{-6}$ mole | $10^{-7}$ mole | $10^{-8}$ mole | $10^{-9}$ mole |
| xanthine | | | | |

PHARMACOLOGICAL TEST 3

(Test of increasing effect of cerebral blood flow)

Increasing effect of cerebral blood flow was measured by a procedure similar to that disclosed in Journal of Surgical Research Vol. 8, No. 10, pages 475–481 (1968). Thus, a bastard dog (male, 12–20 kg of body weight) was fixed in a prone (position) and was anesthetized with 20 ml/kg of pentobarbital sodium and forced to breathe at a frequency of respiration of 20 times/minute. Then, the skull was bared and the surface bone was removed to expose the venous sinus by using a grinder and the venous blood was taken out from the venas which was cannulizated. The amount of venous blood flow was measured by using an electromagnetic blood flow meter and next measured by using dropcounter to measure the number of drops of blood per 10 seconds.

The increasing effect of cerebral blood flow was calculated by comparing the number of blood drops in 30 seconds at the peak of increasement shown before and after the administration of compound to be tested. Each of the compounds to be tested was dissolved in dimethylformamide and diluted with physiological saline solution and administered through a cannule being inserted into the profunda femoris vein.

As to the reference compound, papaverine was used. The results obtained are indicated in Table 4.

TABLE 4

| Compound to be tested | Dosage (μg/kg) | Increasing effect of cerebral blood flow (%) |
|---|---|---|
| 1 | 30 | 36.9 |
| 1 | 300 | 72.2 |
| 3 | 30 | 69.0 |
| 4 | 300 | 65.8 |
| 5 | 300 | 71.0 |
| 6 | 300 | 75.3 |
| 7 | 300 | 68.4 |
| 9 | 300 | 69.9 |
| Papaverine | 1000 | 78.9 |

PHARMACOLOGICAL TEST 4

(Test for hypo-tensive effect)

Hypo-tensive effect of the compounds was measured by determining the maximum blood pressure of the test animals according to a procedure of Tail-cuff method.

The following types of test animals were used:

(1) Gold blatt type renoprival hypertension rats (RHR)

Wistar strain male rats having 160–180 g of body weight were anesthetized with ether and the left-side renal artery was plugged with a silver clip having 0.2 mm inside diameter, while the right-side renal artery was kept as it was without operation. Four (4) weeks after the operation, rats having the maximum blood pressure over 150 mmHg were selected and used as test animals after having been denied food overnight.

(2) Deoxycorticosteroneacetate (DOCA)/saline hypertension rats (DHR)

Wistar strain male rats having 150–170 g of body weight were anesthetized with ether and the left-side kidney was enucleated. One(1) week after the operation, 10 mg/kg of DOCA was injected subcutaneously once a week and 1% NaCl aqueous solution was given as drinking water. Five(5) weeks after the operation, rats having the maximum blood pressure over 150 mmHg were selected and used as test animals after having been denied food overnight.

Each of compounds to be tested was administered orally and the blood pressure of the rats was measured before the administration and 1, 2, 4, 6 and 8 hours after the administration. The results obtained are indicated in Table 5. The blood pressure was measured by using Recorder (Rectihoriz type 8S, San-ei Instrument) and Electrosthygmomanometer PE-300 (Macro Bio-systems, Houston, Tex.).

TABLE 5

| Compound tested (Sample No.) | Dosage (mg/kg) | Number of test runs | Type of rats |
|---|---|---|---|
| 1 | 30 | 5 | RHR |
| 1 | 30 | 5 | DHR |
| 5 | 30 | 5 | RHR |
| 5 | 30 | 5 | DHR |
| 6 | 30 | 4 | RHR |
| 6 | 30 | 4 | DHR |
| 7 | 30 | 4 | RHR |
| 7 | 30 | 4 | DHR |

| Maximum blood pressure (mmHg) | | | | | |
|---|---|---|---|---|---|
| Before the administration* | After the administration** | | | | |
| | 1 hour | 2 hours | 4 hours | 6 hours | 8 hours |
| 211.9 ± 9.2 | −3.3 ± 5.2 | −9.9 ± 6.7 | −36.7 ± 9.7 | −33.4 ± 8.6 | −31.3 ± 8.8 |
| 189.7 ± 8.2 | −10.1 ± 3.7 | −10.0 ± 3.7 | −17.4 ± 5.2 | −25.4 ± 10.5 | −34.6 ± 13.5 |
| 227.6 ± 8.2 | −30.2 ± 8.2 | −21.2 ± 5.7 | −21.7 ± 7.5 | −24.7 ± 10.4 | — |
| 192.7 ± 9.9 | −10.7 ± 10.6 | −15.2 ± 11.2 | −12.5 ± 15.3 | −18.1 ± 9.6 | — |
| 216.9 ± 11.3 | −8.5 ± 4.3 | −10.7 ± 7.6 | −40.8 ± 9.9 | −35.4 ± 9.5 | −28.4 ± 7.7 |
| 170.3 ± 4.9 | −9.2 ± 4.8 | −12.0 ± 5.6 | −18.5 ± 6.1 | −30.3 ± 10.8 | −26.8 ± 10.6 |
| 197.5 ± 8.4 | −9.5 ± 10.4 | −12.6 ± 8.9 | −34.9 ± 19.8 | −30.4 ± 8.6 | −19.7 ± 8.4 |

TABLE 5-continued

| 166.3 ± 2.3 | −8.4 ± 10.3 | −11.5 ± 8.5 | −14.8 ± 7.7 | −20.2 ± 14.0 | −21.3 ± 19.1 |
| --- | --- | --- | --- | --- | --- |

*Mean value ± standard deviation.
**Differencee (mean value ± standard deviation) of the value measured before the administration subtracted by the value measured after the administration at each relevant time period

ACUTE TOXICITY TEST

The test compounds were administered orally to the mice and $LD_{50}$ (mg/kg) of the compounds was determined. The results are shown in Table 6 below.

TABLE 6

|  | Test compound | $LD_{50}$ (mg) Male mice Oral administration |
| --- | --- | --- |
| Compounds of the present invention | 1 | >1000 |
|  | 2 | >1000 |
|  | 3 | >1000 |
|  | 4 | >1000 |
|  | 5 | >1000 |
|  | 6 | >1000 |
|  | 7 | >1000 |
|  | 8 | >1000 |
|  | 9 | >1000 |
|  | 10 | >1000 |
|  | 11 | >1000 |
|  | 12 | >1000 |
|  | 13 | >1000 |
|  | 14 | >1000 |
|  | 15 | >1000 |
|  | 16 | >1000 |

The following reference examples show preparation of compounds which are used as the starting materials in the preparation of the compounds of the present invention.

REFERENCE EXAMPLE 1

Into 200 ml of dried benzene, 30.6 g of N-γ-chlorobutyrylcyclohexylamine was added. While the inside temperature is kept below 20° C. by ice-cooling the outside of the reaction vessel, 30 g of $PCl_5$ was added under stirring condition. After completion of the addition, the stirring is continued for 2 hours at a room temperature, then the reaction mixture is concentrated to a half volume thereof by using an evaporator with a bath temperature of below 50° C. To the concentrated reaction mixture was added dropwise 140 ml of benzene containing 10% of $HN_3$ under stirring condition for 90 minutes while keeping the inside temperature below 15° C. After the addition operation, the reaction mixture is allowed to stand overnight at room temperature. Then the reaction mixture is refluxed for 3 hours with stirring and is concentrated. The thus obtained concentrate is extracted with 200 ml of chloroform. The chloroform layer is washed with 5% $NaHCO_3$ aqueous solution and with water and dried with $Na_2SO_4$. After removal of the drying agent, the mother liquor is concentrated and the residue thus obtained is recrystallized from water-containing isopropanol to obtain 28 g of 1-cyclohexyl-5-γ-chloropropyltetrazole in the form of colorless needle like crystals. Melting point: 82°–85° C.

REFERENCE EXAMPLE 2

By using a method similar to that of REFERENCE EXAMPLE 1, 1-ethyl-5-γ-chloropropyltetrazole is obtained in the form of a colorless liquid having a boiling point of 160° to 163° C./2.0 mmHg.

REFERENCE EXAMPLE 3

Into 150 ml of dried benzene, 17.6 g of N-chloroacetylcyclohexylamine was added. While the inside temperature is kept below 15° C. by ice-cooling the outside of the reaction vessel, 24 g of phosphorus pentachloride ($PCl_5$) was added under stirring condition. After completion of the addition, the stirring is continued for 2 hours at a room temperature, then the reaction mixture is concentrated to a half volume thereof by using an evaporator with a bath temperature of below 50° C. To the concentrated reaction mixture was added dropwise 100 ml of benzene containing 10% of $HN_3$ under stirring condition for 90 minutes while keeping the inside temperature below 15° C. After the addition operation, the reaction mixture is allowed to stand overnight. Then the reaction mixture is refluxed for 3 hours with stirring. The thus obtained concentrate is extracted with 200 ml of chloroform. The chloroform layer is washed with water, 5% $NaHCO_3$ aqueous solution, 5% hydrochloric acid and water in this order and dried with $Na_2SO_4$. After removal of the drying agent by filtration, the mother liquour is concentrated and the residue thus obtained is recrystallized from chloroform-petroleum ether to obtain 16.1 g of 1-cyclohexyl-5-chloromethyltetrazol in the form of colorless needle like crystals. Melting point: 101° to 103.5° C.

REFERENCE EXAMPLES 4 to 13

By using a method similar to that of REFERENCE EXAMPLE 3, there are prepared compounds as follows:

| REFERENCE EXAMPLE NO. | Compound | Crystal form | Melting point (°C.) |
| --- | --- | --- | --- |
| 4 | 1-Benzyl-5-γ-chloropropyltetrazole | Colorless liquid | B.p. 171°–175° C. (1.5 mmHg) |
| 5 | 1-Phenyl-5-γ-chloropropyltetrazole | Colorless liquid | B.p. 205°–210° C. (9 mmHg) |
| 6 | 1-Isopropyl-5-γ-chloropropyltetrazole | Colorless liquid | NMR: $\delta CDCl_3$ . TMS 1.55 (d,6H), 2.3 (m, 2H), 2.95 (t,2H), 3.65(d,2H), 4.7(m, 1H). |
| 7 | 1-Cyclopentyl-5-γ-chloropropyl-tetrazole | Colorless liquid | NMR: $\delta CDCl_3$ . TMS 1.5–2.7(m,10H), 3.1(t,2H), 3.7(t,2H), 4.6–5.0(m,1H) |
| 8 | 1-Cyclohexylmethyl-5- | Colorless | NMR:$\delta CDCl_3$ . TMS |

-continued

| REFERENCE EXAMPLE NO. | Compound | Crystal form | Melting point (°C.) |
|---|---|---|---|
|  | γ-chloropropyltetrazole | liquid | 0.3–2.7(m,13H), 3.5 (t,2H), 3.75(t,2H), 4.15(d,2H) |
| 9 | 1-Cyclooctyl-5-γ-chloropropyltetrazole | Colorless liquid | NMR: δCDCl₃ . TMS 1.35–2.65(m,16H), 3.0(t,2H), 3.67(t, 2H), 4.2–4.7(m,1H) |
| 10 | 1-Cyclohexyl-5-(4-chlorobutyl)-tetrazole | Colorless liquid | NMR: δCDCl₃ . TMS 0.3–2.3(m,14H), 2.6–3.1(m,2H), 3.90–4.50 (m,1H) |
| 11 | 1-Benzyl-5-chloromethyltetrazole | Colorless liquid | NMR:δCDCl₃ . TMS 4.67(s,2H), 5.35(s, 2H), 7.1–7.6(m,5H) |
| 12 | 1-(2-Chloro-4-nitrophenyl)-5-chloromethyltetrazole | Yellowish liquid | NMR:δCDCl₃ . TMS. 4.8(s,2H), 7.76(d, 1H), 8.25–8.60(m,2H) |
| 13 | 1-(4-Ethylphenyl)-5-chloromethyltetrazole | Colorless liquid | NMR:δCDCl₃ . TMS. 1.3(t,3H), 2.75(q, 2H), 4.8(s,2H), 7.43(s,4H) |

The process for producing the compounds of the present invention will now be described in the following examples:

EXAMPLE 1

Into 200 ml of dimethylformamide, 3.2 g of 6-hydroxycarbostyril, 3.3 g of potassium carbonate and 7.7 g of 1-cyclohexyl-5-γ-chloropropyltetrazole are added and stirred for 4 hours at 70° to 80° C. After the reaction is completed, dimethylformamide is removed by distillation under reduced pressure. The residue thus obtained is then extracted with 300 ml of chloroform and the chloroform layer is washed with a diluted NaOH aqueous solution and with water and next dried with Na₂SO₄. After removal of the drying agent by filtration, then the mother liquor is concentrated and the residue is recrystallized from chloroform to obtain 3.54 g of 6-[3-(1-cyclohexyltetrazol-5-yl)propoxy]carbostyril, in the form of colorless needle-like crystals. Melting point: 211° to 212° C.

EXAMPLE 2

By using a method similar to that in Example 1, 6-[3-(1-ethyltetrazol-5-yl)propoxy]carbostyril is prepared in the form of pale yellowish powdery crystals. Melting point: 179°–181.5° C.

EXAMPLE 3

Into 100 ml of isopropanol, 2.63 g of 6-hydroxy-1-methylcarbostyril and 2.64 ml of 1,5-diazabicyclo[5,4,0]undecene-5 (DBU) are added and refluxed under stirring. Then 100 ml of isopropanol solution containing 5.7 g of 1-cyclohexyl-5-γ-iodopropyltetrazole is added dropwise for 90 minutes. After completion of the addition, the reaction mixture is further refluxed with stirring for 5 hours and then concentrated. The residue is extracted with 300 ml of chloroform and the chloroform layer is washed with a diluted NaOH aqueous solution, and a diluted hydrochloric acid. After drying with Na₂SO₄, chloroform is removed by distillation and the residue obtained is recrystallized from acetone, to obtain 4.8 g of 1-methyl-6-[3-(1-cyclohexyltetrazol-5-yl)propoxy]carbostyril in the form of colorless needle-like crystals. Melting point: 150°–151.5° C.

EXAMPLE 4

Into 100 ml of ethanol, 3.22 g of 6-hydroxycarbostyril and 3.51 ml of 1,5-diazabicyclo[5,4,0]-undecene-5 (DBU) are added and refluxed under stirring. Then 100 ml of ethanol containing 7 g of 1-benzyl-5-γ-iodopropyltetrazole is added dropwise for 90 minutes. After completion of the addition, the reaction mixture is further refluxed for 5 hours and then concentrated. The residue is extracted with 300 ml of chloroform and the chloroform layer is washed with a diluted NaOH aqueous solution, a diluted hydrochloric acid and water and dried with Na₂SO₄. After the removal of the solvent, the residue is recrystallized from water-containing ethanol to obtain 4 g of 6-[3-(1-benzyltetrazol-5-yl)propoxy]carbostyril in the form of colorless needle-like crystals. Melting point: 152°–154° C.

EXAMPLES 5 to 41

By using a method similar to that of Example 4, there are prepared compounds as follows:

| EXAMPLE No. | Compound | Crystal form | Melting point (°C.) |
|---|---|---|---|
| 5 | 4-[3-(1-Cyclohexyltetrazol-5-yl)propoxy]carbostyril | Colorless needle-like crystals | 247–249° C. |
| 6 | 5-[3-(1-Benzyltetrazol-5-yl)propoxy]-3,4-dihydrocarbostyril | Colorless needle-like crystals | 172–172.5° C. |
| 7 | 5-(1-Cyclohexyltetrazol-5-yl-methoxy)-3,4-dihydrocarbostyril | Colorless needle-like crystals | 219.5–221° C. |
| 8 | 1-Benzoyl-5-(1-cyclohexyltetrazol-5-yl-methoxy)-3,4-dihydrocarbostyril | Colorless needle-like crystals | 156–157° C. |
| 9 | 5-[3-(1-Cyclohexyltetrazol-5-yl)propoxy]-3,4-dihydrocarbostyril | Colorless needle-like crystals | 220–221.5° C. |
| 10 | 5-[3-(1-Cyclopentyltetrazol-5-yl)propoxy]-3,4-dihydrocarbostyril | Colorless needle-like crystals | 199.5–200° C. |
| 11 | 6-(1-Cyclohexyltetrazol-5-yl-methoxy)carbostyril | Colorless needle-like crystals | 278–281° C. |
| 12 | 6-[3-(1-Phenyltetrazol-5-yl)propoxy]carbostyril | Colorless needle-like crystals | 173–174° C. |

| EX-AM-PLE No. | Compound | Crystal form | Melting point (°C.) |
|---|---|---|---|
| 13 | 4-Methyl-6-[3-(1-cyclohexyltetrazol-5-yl)-propoxy]carbostyril | Colorless needle-like crystals | 226–228° C. |
| 14 | 6-(1-Benzyltetrazol-5-yl-methoxy)carbostyril | Colorless needle-like crystals | 233.5–235° C. |
| 15 | 6-[3-(1-Cyclohexylmethyltetrazol-5-yl)propoxy]-carbostyril | Colorless needle-like crystals | 175–175.5° C. |
| 16 | 6-[3-(1-Cyclooctyltetrazol-5-yl)propoxy]carbostyril | Colorless needle-like crystals | 220–220.5° C. |
| 17 | 6-[3-(1-Cyclopentyltetrazol-5-yl)propoxy]carbostyril | Colorless needle-like crystals | 196.5–197.5° C. |
| 18 | 6-[4-(1-Cyclohexyltetrazol-5-yl)butoxy]carbostyril | Colorless needle-like crystals | 177.5–178.5° C. |
| 19 | 1-Benzyl-6-[3-(1-cyclohexyltetrazol-5-yl)propoxy]-carbostyril | Colorless needle-like crystals | 139–140° C. |
| 20 | 1-Allyl-6-[3-(1-cyclohexyltetrazol-5-yl)propoxy]-carbostyril | Colorless needle-like crystals | 102–103.5° C. |
| 21 | 6-[3-(1-Cyclohexyltetrazol-5-yl)propoxy]-3,4-dihydrocarbostyril | Colorless needle-like crystals | 154.5–155.5 |
| 22 | 1-Acetyl-6-[3-(1-cyclohexyltetrazol-5-yl)propoxy]-3,4-dihydrocarbostyril | Colorless needle-like crystals | 124–126.5 |
| 23 | 6-[3-(1-Benzyltetrazol-5-yl)-propoxy]-3,4-dihydro-carbostyril | Colorless needle-like crystals | 136.5–138 |
| 24 | 6-[3-(1-Phenyltetrazol-5-yl)-propoxy]-3,4-dihydro-carbostyril | Colorless needle-like crystals | 159–160.5 |
| 25 | 6-[3-(1-Cyclohexylmethyltetrazol-5-yl)propoxy]-3,4-dihydrocarbostyril | Colorless needle-like crystals | 137–138° C. |
| 26 | 6-[4-(1-Cyclohexyltetrazol-5-yl)butoxy]3,4-dihydrocarbostyril | Colorless needle-like crystals | 148–150.5° C. |
| 27 | 1-Propionyl-6-(1-benzyltetrazol-5-yl-methoxy)-3,4-dihydrocarbostyril | Colorless syrupy liquid | NMR:δCDCl₃ (TMS) 1.2(t, 3H), 2.35–3.25 (m,6H), 5.2(s, 2H),5.65(s,2H), 6.6–6.9(m,2H), 7.0–7.5(m,6H) |
| 28 | 1-Ethyl-6-[3-(1-cyclohexyltetrazol-5-yl)propoxy]-3,4-dihydrocarbostyril | Colorless plate-like crystals | 105.6–108.5° C. |
| 29 | 6-[1-(2-Chloro-4-nitrophenyl)-tetrazol-5-yl-methoxy]-3,4-dihydrocarbostyril | Yellowish grain-like crystals | 214.5–216° C. (decomp.) |
| 30 | 6-[1-(4-Ethylphenyl)tetrazol-5-yl-methoxy]3,4-dihydro-carbostyril | Colorless needle-like crystals | 149–149.5° C. |
| 31 | 1-(3,4,5-Trimethoxybenzoyl)-6-[3-(1-cyclohexyltetrazol-5-yl)propoxy]-3,4-dihydrocarbostyril | Colorless needle-like crystals | 57–59° C. |
| 32 | 6-[3-(1-Isopropyltetrazol-5-yl)propoxy]carbostyril | Colorless needle-like crystals | 202–203° C. |
| 33 | 7-[3-(1-Cyclohexyltetrazol-5-yl)propoxy]-3,4-dihydrocarbostyril | Colorless needle-like crystals | 171.5–173.5° C. |
| 34 | 7-[3-(1-Phenyltetrazol-5-yl)-propoxy-]3,4-dihydro-carbostyril | Colorless plate-like crystals | 159–161.5° C. |
| 35 | 4-Methyl-7-[3-(1-cyclohexyltetrazol-5-yl)propoxy]-carbostyril | Colorless needle-like crystals | 236–238° C. |
| 36 | 7-(1-Benzyltetrazol-5-yl-methoxy)-3,4-dihydrocarbostyril | Colorless grain-like crystals | 178.5–180° C. |
| 37 | 8-(1-Cyclohexyltetrazol-5-yl-methoxy)carbostyril | Colorless needle-like crystals | 216–217° C. |
| 38 | 8-[3-(1-Cyclohexyltetrazol-5-yl)propoxy]-3,4-dihydro-carbostyril | Colorless needle-like crystals | 164.5–166° C. |
| 39 | 8-[3-(1-Cyclooctyltetrazol-5-yl)propoxy]-3,4-dihydro-carbostyril | Colorless grain-like crystals | 145–146° C. |
| 40 | 8-[3-(1-Isopropyltetrazol-5-yl)propoxy]carbostyril | Colorless needle-like crystals | 174–176° C. |
| 41 | 6-(1-Benzyltetrazol-5-yl-methoxy)-3,4-dihydro-carbostyril | Colorless needle-like crystals | a165–167° C. |

EXAMPLE 42

3.2 Grams of 6-[3-(1-cyclohexyltetrazol-5-yl)propoxy]-3,4-dihydrocarbostyril and 3.4 g of 90% DDQ are added to 100 ml of dioxane and this mixture is refluxed for 9.5 hours and then cooled. After the reaction is completed, the solvent is distilled off and the residue obtained is dissolved in chloroform and the organic layer is washed with aqueous saturated NaHCO₃ solution, and with water then dried with Na₂SO₄ and treated with an activated charcoal. After the solvent is removed by distillation, the resultant residue is refined by silica gel column chromatography [silica gel: Wakogel- C-200; eluent:chloroform:methanol = 10:1 (V/V)] and the crude crystals are recrystallized from chloroform to obtain 1.1 g of 6-[3-(1-cyclohexyltetrazol-5-yl)propoxy]carbostyril in the form of colorless needle-like crystals. Melting point: 211°–212° C.

EXAMPLE 43

Into 500 ml of methanol, 2.5 g of 6-[3-(1-cyclohexyltetrazol-5-yl)propoxy]carbostyril is added, then 0.1 of palladium black is added into the mixture and the reaction is carried out under 2.5 atoms of H₂-pressure at 50° C. for 8 hours. After the reaction is completed, the catalyst is removed by filtration and the filtrate is concentrated to dryness. The residue is recrystallized from chloroform-petroleum ether to obtain 1.5 g of 6-[3-(1-cyclohexyltetrazol-5-yl)propoxy]-3,4-dihydrocarbostyril in the form of colorless needle-like crystals. Melting point: 154.4°–155.5° C.

EXAMPLE 44

Into 30 ml of dimethylformamide, 1.8 g of 6-[3-(1-cyclohexyltetrazol-5-yl)propoxy]-3,4-dihydrocarbostyril is dissolved and 0.14 g of NaH is added under stirring by ice-cooling the outside of the reaction vessel for 1 hour.

Into this reaction mixture, 0.41 ml of acetyl chloride is added dropwise. After completion of the addition, the reaction mixture is stirred for 2 hours at a room temperature. Then the reaction mixture is extracted with chloroform (three times with each 100 ml of chloroform). The chloroform layer is washed with saturated sodium chloride solution thoroughly and dried with Na₂SO₄. After chloroform is removed by distillation, the residue is purified by a silica gel column chromatography (eluent: ethyl acetate). The fraction coming out at the first is separated and concentrated, then recrystallized from chloroform-petroleum ether to obtain 1.1 g of 1-acetyl- 6-[3-(1-cyclohexyltetrazol-5-yl)propoxy]-3,4-dihydrocarbostyril in the form of colorless needle-like crystals. Melting point: 124°-126.5° C.

EXAMPLES 45 to 47

By using a method similar to that of Example 44, there are obtained compounds as follows:

| Example NO. | Compound | Crystal form | Melting point (°C.) |
|---|---|---|---|
| 45 | 1-Benzoyl-5-(1-cyclohexyl-tetrazol-5-yl-methoxy)-3,4-dihydrocarbostyril | Colorless needle-like crystals | 156-157° C. |
| 46 | 1-(3,4,5-Trimethoxybenzoyl)-6-[3-(1-cyclohexyltetrazol-5-yl)-propoxy]-3,4-dihydrocarbostyril | Colorless needle-like crystals | 57-59° C. |
| 47 | 1-Propionyl-6-(1-benzyl-tetrazol-5-yl-methoxy)-3,4-dihydrocarbostyril | Colorless syrupy liquid | NMR:δCDCl₃ (TMS):1.2(t, 3H),2.35-3.25 (m,6H),5.2(s, 2H),5.65(s,2H), 6.6-6.9(m,2H), 7.0-7.5(m,6H) |

EXAMPLE 48

Into 50 ml of dimethylformamide, 1.8 g of 6-[3-(1-cyclohexyltetrazol-5-yl)propoxy]carbostyril is dissolved, then 0.15 g of NaH is added under stirring for 30 minutes by ice-cooling the outside of the reaction vessel. Into the reaction mixture, 0.52 ml of allyl bromide is added dropwise and stirred at a room temperature for 2 hours. The reaction mixture is then concentrated and the residue is extracted with chloroform, washed with water and dried with Na₂SO₄. After removal of the drying agent by filtration, the mother liquor is concentrated and the residue is dissolved in chloroform. The chloroform solution is washed with water and then concentrated. The residue thus obtained is purified by a silica gel column chromatography [eluent: chloroform-methanol (50:1)]. The eluted solution is concentrated and the residue is recrystallized from chloroform-petroleum ether to obtain 1.2 g of 1-allyl-6-[3-(1-cyclohexyltetrazol-5-yl)propoxy]carbostyril in the form of colorless needle-like crystals. Melting point: 102°-103.5° C.

EXAMPLES 49 to 51

By using a method similar to that of Example 48, there are obtained compounds as follows:

| EXAMPLE NO. | Compound | Crystal form | Melting point (°C.) |
|---|---|---|---|
| 49 | 1-Methyl-6-[3-(1-cyclohexyl-tetrazol-5-yl)propoxy]-carbostyril | Colorless needle-like crystals | 150-151.5° C. |
| 50 | 1-Benzyl-6-[3-(1-cyclohexyl-tetrazol-5-yl)propoxy]-carbostyril | Colorless needle-like crystals | 139-140° C. |
| 51 | 1-Ethyl-6[3-(1-cyclohexyl-tetrazol-5-yl)propoxy]-3,4-dihydrocarbostyril | Colorless plate-like crystals | 106.5-108.5° C. |

EXAMPLES 52 to 54

By using a method similar to that of Example 4, there are obtained compounds as follows:

| EX. NO. | Compound | Crystal form | Melting point (°C.) |
|---|---|---|---|
| 52 | 6-{3-[1-(β-3,4-Dimethoxy-phenethyl)tetrazol-5-yl]-propoxy}carbostyril | Colorless leaf-like crystals | 206-208° C. |
| 53 | 6-{3-[1-(β-3,4-Methylene-dioxyphenethyl)tetrazol-5-yl]propoxy}carbostyril | | |
| 54 | 6-{3-[1-(β-4-Dimethylamino-phenethyl)tetrazol-5-yl]-propoxy}carbostryil | | |

What is claimed is:

1. A compound of the general formula,

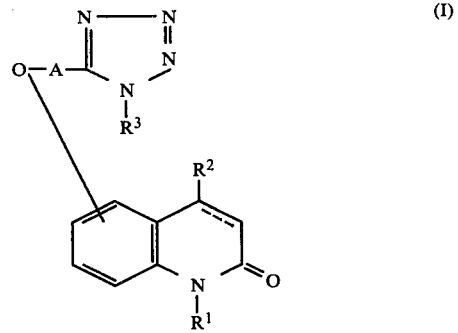

wherein $R^1$ is a hydrogen atom, a lower alkyl group, a lower alkenyl group, a lower alkanoyl group, a benzoyl group or a phenyl-$C_{1-4}$ alkyl group; $R^2$ is a hydrogen atom, a lower alkyl group or a group of the formula

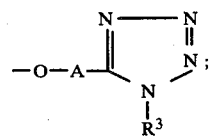

$R^3$ is a lower alkyl group, a $C_{3-8}$ cycloalkyl group, a $C_{3-8}$ cycloalkyl-$C_{1-4}$ alkyl group, a phenyl group or a phenyl-$C_{1-4}$ alkyl group; A is a lower alkylene group; the carbon-carbon bond between 3- and 4-positions in the carbostyril skeleton is either single or double bond; and the substituted position of the group represented by the formula,

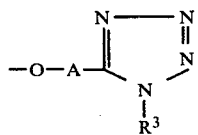

in the carbostyril skeleton is either 4-, 5-, 6-, 7- or 8-position provided that only one such group of the formula can be substituted in the whole carbostyril skeleton, thus when $R^2$ in 4-position is

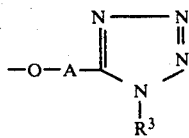

then 5-, 6-, 7- or 8-position will have no such substituted group; furthermore, the phenyl group in the above-mentioned benzoyl group, phenyl-$C_{1-4}$ alkyl group or phenyl group may have substituted group(s) selected from the group consisting of lower alkoxy, lower alkyl, halogen, di-lower alkylamino, nitro, and lower alkenedioxy.

2. A compound of the general formula (I) according to claim 1, wherein the substituted position of the group of the formula

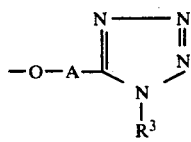

is 5-position of the carbostyril skeleton.

3. A compound of the general formula (I) according to claim 2, wherein $R^3$ is a $C_{3-8}$ cycloalkyl group or a $C_{3-8}$ cycloalkyl-$C_{1-4}$ alkyl group.

4. A compound of the general formula (I) according to claim 2, wherein $R^3$ is a phenyl-$C_{1-4}$ alkyl group which may have substituted group(s) selected from the group consisting of lower alkoxy, lower alkyl, halogen, di-lower alkylamino, nitro, and lower alkenedioxy, a phenyl group which may have substituted group(s) selected from the group consisting of lower alkoxy, lower alkyl, halogen, di-lower alkylamino, nitro, and lower alkenedioxy or a lower alkyl group.

5. A compound of the general formula (I) according to claim 1, wherein the substituted position of the group of the formula

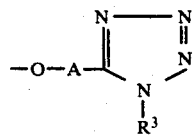

is 6-position of the carbostyril skeleton.

6. A compound of the general formula (I) according to claim 5, wherein $R^3$ is a $C_{3-8}$ cycloalkyl group or a $C_{3-8}$ cycloalkyl-$C_{1-4}$ alkyl group.

7. A compound of the general formula (I) according to claim 5, where $R^3$ is a phenyl-$C_{1-4}$ alkyl group which may have substituted group(s) selected from the group consisting of lower alkoxy, lower alkyl, halogen, di-lower alkylamino, nitro, and lower alkenedioxy, a phenyl group which may have substituted group(s) selected from the group consisting of lower alkoxy, lower alkyl, halogen, di-lower alkylamino, nitro, and lower alkenedioxy, or a lower alkyl group.

8. A compound of the general formula (I) according to claim 1, wherein the substituted position of the group of the formula

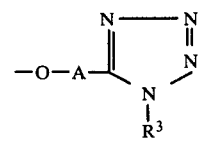

is 4-, 7- or 8-position of the carbostyril skeleton.

9. A compound of the general formula (I) according to claim 8, wherein $R^3$ is a $C_{3-8}$ cycloalkyl group or a $C_{3-8}$ cycloalkyl-$C_{1-4}$ alkyl group.

10. A compound of the general formula (I) according to claim 8, where $R^3$ is a phenyl-$C_{1-4}$ alkyl group which may have substituted group(s) selected from the group consisting of lower alkoxy, lower alkyl, halogen, di-lower alkylamino, nitro, and lower alkenedioxy, a phenyl group which may have substituted group(s) selected from the group consisting of lower alkoxy, lower alkyl, halogen, di-lower alkylamino, nitro, and lower alkenedioxy or a lower alkyl group.

11. 6-[3-(1-Cyclohexyltetrazol-5-yl)propoxy]carbostyril.

12. 6-[3-(1-Benzyltetrazol-5-yl)propoxy]carbostyril.

13. 5-[3-(1-Cyclohexyltetrazol-5-yl)propoxy]-3,4-dihydrocarbostyril.

14. 6-[3-(1-Phenyltetrazol-5-yl)propoxy]carbostyril.

15. 4-Methyl-6-[3-(1-cyclohexyltetrazol-5-yl)propoxy]carbostyril.

16. 6-[3-(1-Cyclohexylmethyltetrazol-5-yl)propoxy]carbostyril.

17. 6-[3-(1-Cyclooctyltetrazol-5-yl)propoxy]-carbostyril.

18. 6-[3-(1-Cyclopentyltetrazol-5-yl)propoxy]-carbostyril.

19. 6-[4-(1-Cyclohexyltetrazol-5-yl)butoxy]carbostyril.

20. 6-[3-(1-Cyclohexyltetrazol-5-yl)propoxy]-3,4-dihydrocarbostyril.

21. 6-[3-(1-Cyclohexylmethyltetrazol-5-yl)propoxy]-3,4-dihydrocarbostyril.

22. 7-[3-(1-Cyclohexyltetrazol-5-yl)propoxy]-3,4-dihydrocarbostyril.

23. 8-[3-(1-Cyclohexyltetrazol-5-yl)propoxy]-3,4-dihydrocarbostyril.

24. 4-[3-(1-Cyclohexyltetrazol-5-yl)propoxy]-carbostyril.

25. A platelet aggregation inhibitor composition containing as an active ingredient a pharmacologically effective amount of a compound of the formula (I) of claim 1 and a pharmaceutically acceptable carrier.

26. A phosphodiesterase inhibitor composition containing as an active ingredient a pharmacologically effective amount of a compound of the formula (I) of claim 1 and a pharmaceutically acceptable carrier.

27. A cerebral blood flow improver composition containing as an active ingredient a pharmacologically effective amount of a compound of the formula (I) of claim 1 and a pharmaceutically acceptable carrier.

28. An anti-hypertensive agent composition containing as an active ingredient a pharmacologically effective amount of a compound of the formula (I) of claim 1 and a pharmaceutically acceptable carrier.

* * * * *